United States Patent
Nichols et al.

(10) Patent No.: US 6,854,461 B2
(45) Date of Patent: Feb. 15, 2005

(54) AEROSOL GENERATOR FOR DRUG FORMULATION AND METHODS OF GENERATING AEROSOL

(75) Inventors: Walter A. Nichols, Chesterfield, VA (US); Donald L. Brookman, Richmond, VA (US); Gary E. Grollimund, Chesterfield, VA (US); Ulysses Smith, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 78 days.

(21) Appl. No.: 10/418,101

(22) Filed: Apr. 18, 2003

(65) Prior Publication Data

US 2004/0025865 A1 Feb. 12, 2004

Related U.S. Application Data

(60) Provisional application No. 60/379,025, filed on May 10, 2002.

(51) Int. Cl.[7] ............................................. A61M 15/00
(52) U.S. Cl. .............................. 128/203.16; 128/203.17
(58) Field of Search ....................... 128/200.14, 200.21, 128/200.24, 203.12, 203.16, 203.17, 203.14, 203.15, 203.26, 203.27, 203.28, 204.17, 205.13, 205.15, 205.16; 222/52, 57, 67, 92, 95; 239/302, 304, 320, 321, 329

(56) References Cited

U.S. PATENT DOCUMENTS

| | | |
|---|---|---|
| 3,162,324 A | 12/1964 | Houser |
| 3,486,663 A | 12/1969 | Humphrey |
| 3,847,304 A | 11/1974 | Cohen |
| 3,902,635 A | 9/1975 | Jinotti |
| 3,904,083 A | 9/1975 | Little |
| 3,987,941 A | 10/1976 | Blessing |
| 4,042,153 A | 8/1977 | Callahan et al. |
| 4,077,542 A | 3/1978 | Petterson |
| 4,162,501 A | 7/1979 | Mitchell et al. |
| 4,231,492 A | 11/1980 | Rios |
| 4,261,356 A | 4/1981 | Turner et al. |
| 4,391,308 A | 7/1983 | Steiner |
| 4,433,797 A | 2/1984 | Galia |
| 4,471,892 A | 9/1984 | Coleman |
| 4,627,432 A | 12/1986 | Newell et al. |
| 4,811,731 A | 3/1989 | Newell et al. |
| 4,974,754 A | 12/1990 | Wirz |
| 5,096,092 A | 3/1992 | Devine |
| 5,178,305 A | 1/1993 | Keller |
| 5,230,445 A | 7/1993 | Rusnak |
| 5,421,489 A | 6/1995 | Holzner et al. |
| 5,487,378 A | 1/1996 | Robertson et al. |
| 5,522,378 A | 6/1996 | Ritson et al. |
| 5,617,844 A | 4/1997 | King |
| 5,622,162 A | 4/1997 | Johansson et al. |

(List continued on next page.)

OTHER PUBLICATIONS

Notification of Transmittal of the International Search Report or the Declaration for PCT/US03/12065 dated Oct. 8, 2003.
Notification of Transmittal of International Preliminary Examination Report dated Jul. 29, 2004 for PCT/US03/12065.

Primary Examiner—Henry Bennett
Assistant Examiner—Teena Mitchell
(74) Attorney, Agent, or Firm—Burns, Doane, Swecker & Mathis LLP

(57) ABSTRACT

An aerosol generator and methods of delivering aerosol to a user inhaling on a mouthpiece when a pressure drop is detected within the mouthpiece are disclosed. A medicated fluid passing through a capillary passage is heated to vaporize the fluid and form the aerosol by condensation or mixture of the vaporized fluid with admixed air. A metering chamber allows consistent delivery of precise doses of fluid to the capillary passage. Once the pressure drop is detected, aerosol can be quickly delivered to the user as the user begins to inhale on the mouthpiece. The quick delivery of aerosol provides more efficient use of the user's lung capacity.

46 Claims, 12 Drawing Sheets

U.S. PATENT DOCUMENTS

| | | |
|---|---|---|
| 5,682,874 A | 11/1997 | Grabenkort |
| 5,743,251 A | 4/1998 | Howell et al. |
| 5,765,724 A | 6/1998 | Amberg et al. |
| 5,794,612 A | 8/1998 | Wachter et al. |
| 5,839,430 A | 11/1998 | Cama |
| 5,881,714 A | 3/1999 | Yokoi et al. |
| 5,894,841 A | 4/1999 | Voges |
| 5,970,974 A | 10/1999 | Van Der Linden et al. |
| 6,095,134 A | 8/2000 | Sievers et al. |
| 6,152,130 A | 11/2000 | Abrams et al. |
| 6,164,630 A | 12/2000 | Birdsell et al. |
| 6,205,999 B1 | 3/2001 | Ivri et al. |
| 6,206,242 B1 | 3/2001 | Amberg |
| 6,223,746 B1 | 5/2001 | Jewett et al. |
| 6,230,706 B1 | 5/2001 | Gonda et al. |
| 6,234,167 B1 | 5/2001 | Cox et al. |
| 6,276,347 B1 | 8/2001 | Hunt |
| 6,321,747 B1 | 11/2001 | Dmitrovic et al. |
| 6,516,796 B1 * | 2/2003 | Cox et al. ............... 128/200.23 |
| 6,528,018 B1 | 3/2003 | Berndt |
| 6,568,390 B2 * | 5/2003 | Nichols et al. ......... 128/203.16 |
| 6,772,757 B2 * | 8/2004 | Sprinkel, Jr. ............ 128/203.26 |

* cited by examiner

US 6,854,461 B2

AEROSOL GENERATOR FOR DRUG FORMULATION AND METHODS OF GENERATING AEROSOL

This application claims the benefit of Provisional application No. 60/379,025, filed May 10, 2002.

BACKGROUND

Metered dose inhalers for delivering aerosol medication for inhalation by a user are disclosed in U.S. Pat. Nos. 5,487,378; 5,522,378; 5,622,162; 5,794,612; 5,839,430; 5,894,841; and 6,152,130. Commonly owned U.S. Pat. Nos. 5,743,251 and 6,234,167 disclose aerosol generators that vaporize a liquid formulation to form an inhalation aerosol.

Other techniques are known for generating aerosols. For example, U.S. Pat. Nos. 4,811,731 and 4,627,432 disclose devices for administering medicaments to patients in which a capsule is pierced by a pin to release a medicament in powder form.

SUMMARY

An exemplary embodiment of an aerosol generator comprises a reservoir containing a liquid; a flow passage in fluid communication with the reservoir; and a heater arranged to heat the liquid in the flow passage to produce a vapor. The vapor admixes with air to produce an aerosol. In the embodiment: a) the reservoir comprises a chamber, a liquid stored in a bladder in the chamber, and a free weight, which compresses the bladder such that the liquid can be subjected to substantially constant pressure; b) the reservoir is removably attachable to a fluid delivery assembly of the aerosol generator; c) the flow passage is defined by an elastomeric member, which comprises at least a first depression defining a metering chamber, with the first depression sized to contain a predetermined volume of the liquid; and/or d) the flow passage is defined by the elastomeric member, which comprises a first depression defining a metering chamber, a second depression defining an inlet valve, and a third depression defining an outlet valve.

Another exemplary embodiment of the aerosol generator comprises a reservoir including a chamber; a liquid stored in a bladder in the chamber; and a free weight, which compresses the liquid such that the liquid can be subjected to substantially constant pressure. The aerosol generator also comprises a flow passage in fluid communication with the reservoir, and a heater disposed to heat a portion of the flow passage to produce a vapor. The vapor admixes with air to produce an aerosol.

A further exemplary embodiment of the aerosol generator comprises a reservoir containing a liquid. The reservoir is removably attachable to a fluid delivery assembly of the aerosol generator. The fluid delivery assembly includes a fluid passage and a heater. The fluid passage is in fluid communication with the reservoir, and the heater is arranged to heat the liquid in the fluid passage to create a vapor, which admixes with air to produce an aerosol.

Another exemplary embodiment of the aerosol generator comprises a reservoir containing a liquid and a flow passage in fluid communication with the reservoir. The flow passage is defined at least in part by an elastomeric member, which includes a depression defining a metering chamber sized to contain a predetermined volume of the liquid. The aerosol generator also comprises a capillary passage in fluid communication with the metering chamber, and a heater arranged relative to the capillary passage so as to heat at least a portion of the capillary passage sufficiently to volatilize liquid contained in the portion of the capillary passage.

Another exemplary embodiment of the aerosol generator comprises a reservoir containing a liquid, and a flow passage in fluid communication with the reservoir. The flow passage is defined at least in part by an elastomeric member, which comprises first, second and third depressions. The first depression comprises an inlet valve, the second depression comprises an outlet valve, and the third depression defines a metering chamber sized to contain a predetermined volume of the liquid. The aerosol generator also comprises a capillary passage in fluid communication with the metering chamber, and a heater arranged relative to the capillary passage so as to heat at least a portion of the capillary passage sufficiently to volatilize liquid contained in the portion of the capillary passage.

DETAILED DESCRIPTION

An aerosol generator and methods of generating an aerosol with the aerosol generator are described herein. The aerosol generator can be provided in various different constructions and sizes, such as in a hand-held inhaler. In a preferred embodiment, aerosol is delivered to a user by inhaling on a mouthpiece when a pressure drop is detected within the aerosol generator. A medicated fluid is flowed through a capillary passage and heated sufficiently to vaporize the fluid and form the aerosol by mixture of the vaporized fluid with air. The aerosol generator includes a metering chamber, which allows the consistent delivery of precise doses of fluid to the capillary passage. Once the pressure drop is detected, the aerosol can be delivered quickly to the user as the user inhales on the mouthpiece. The quick delivery of aerosol provides efficient use of the user's lung capacity.

An aerosol generator in accordance with an exemplary preferred embodiment comprises a mouthpiece, a pressure sensor, and a fluid delivery assembly capable of delivering controlled amounts of an aerosolized drug formulation to a user. During operation, when a user inhales on the mouthpiece of the aerosol generator, the pressure sensor senses a pressure drop. The pressure sensor sends a signal to a controller, which activates a drive assembly including a motor, which rotates a camshaft operatively coupled with elements of the fluid delivery assembly, including actuators for an inlet valve, a metering chamber, and an outlet valve. As the camshaft rotates, fluid is caused to flow from the metering chamber into a heated capillary passage in which the fluid is volatilized. The volatilized fluid exits the capillary passage into the interior of the mouthpiece, where ambient air mixes with the volatilized fluid and produces an aerosol inhaled by the user.

Figure 1:
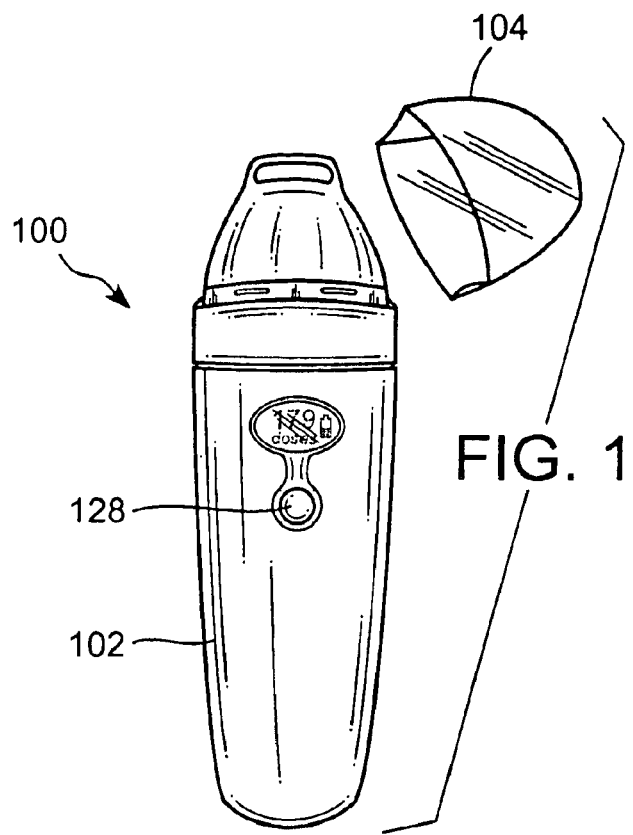
FIG. 1 is a perspective view of an aerosol generator in accordance with an embodiment, showing the cap removed.
Figure 2:
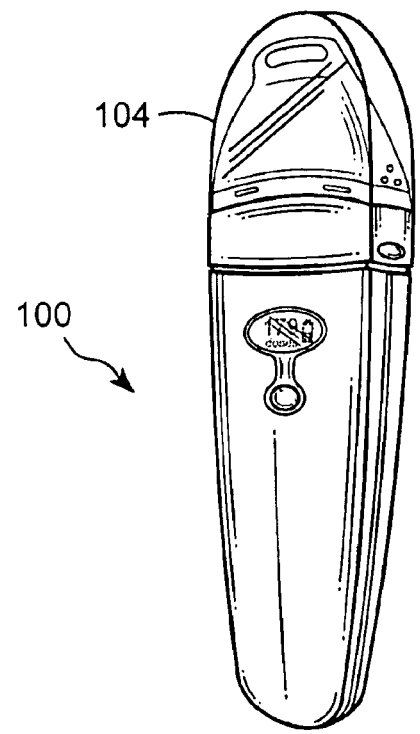
FIG. 2 shows the aerosol generator of FIG. 1 with the cap installed.
Figure 3:
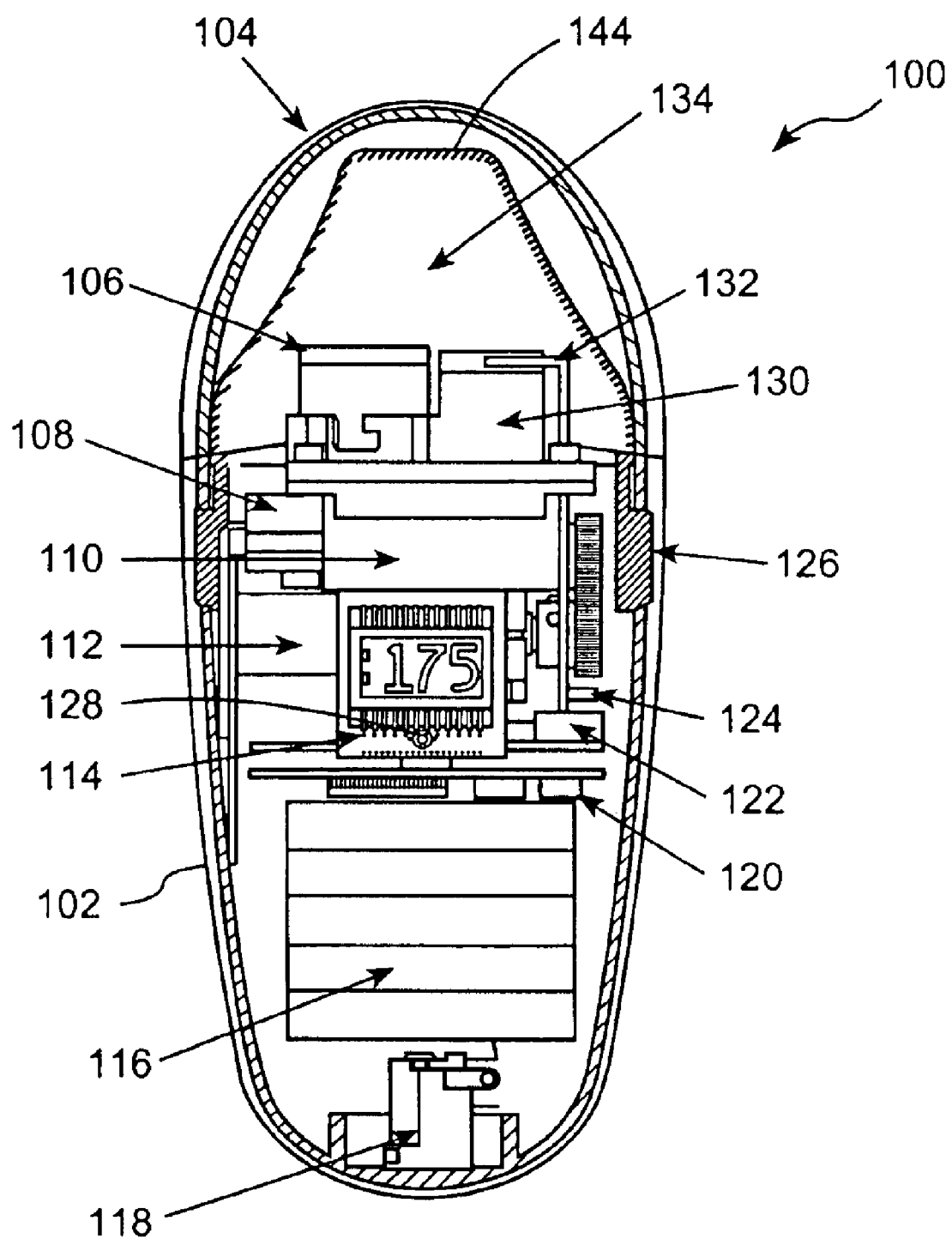
FIG. 3 illustrates components of an aerosol generator in accordance with an embodiment.

FIGS. 1–3 illustrate an exemplary embodiment of an aerosol generator 100 in accordance with a first embodiment. The aerosol generator 100 includes a housing 102; a removable protective cap 104 including a master on/off switch, such as a Hall-effect switch (not shown); a fluid delivery assembly 110 including a reservoir 106 and a heater 130; a Hall-effect transducer 108; a drive assembly 112; a display 114; a battery unit 116; a charging jack 118; control electronics 120; a pressure sensor 122; an air inlet 124; a release 126 for detaching the fluid delivery assembly 110 and/or the drive assembly 112 from the aerosol generator; an activation switch 128; an air passage 132 and a removable mouthpiece 134. FIG. 1 shows the cap 104 removed from the aerosol generator 100, while FIG. 2 shows the cap installed on the aerosol generator.

The housing 102, cap 104 and mouthpiece 134 are preferably made of a polymer material. These parts may be fabricated by plastic injection molding, or any other suitable technique. The housing 102 can be fabricated in an ergonmetric configuration that is comfortable to hold by a user.

Figure 4:
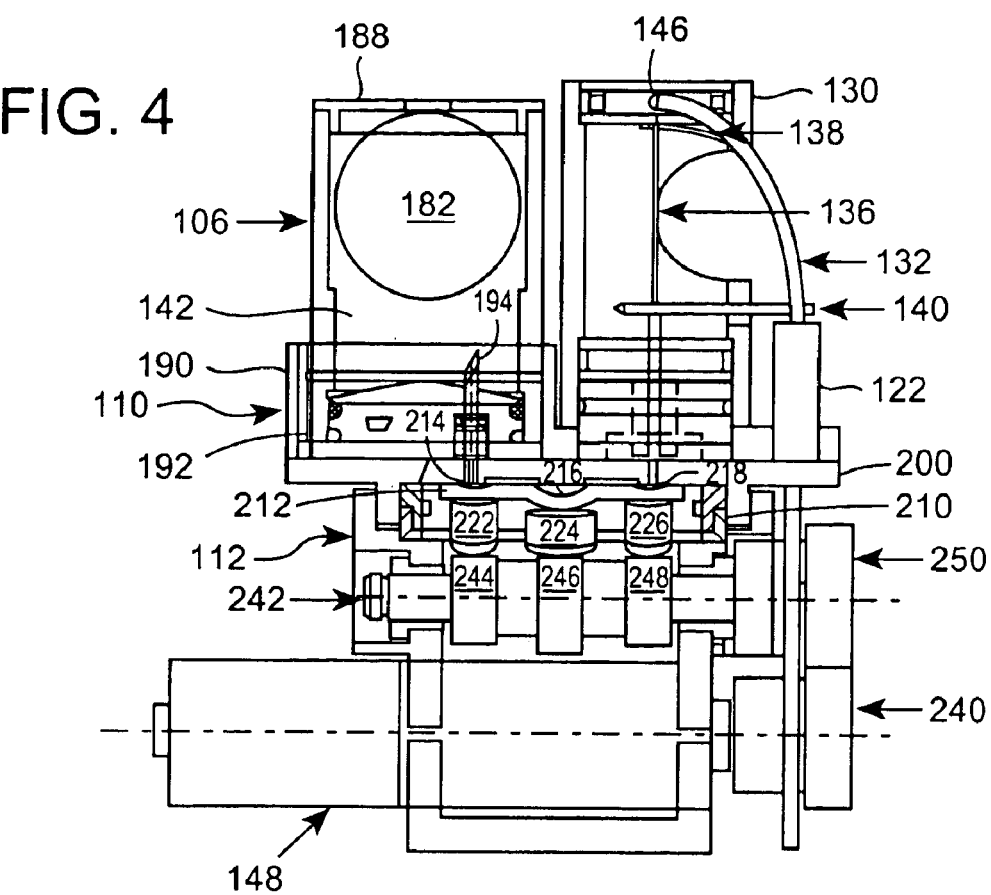
FIG. 4 illustrates a fluid delivery assembly attached to a drive assembly of an aerosol generator in accordance with an embodiment.
Figure 5:
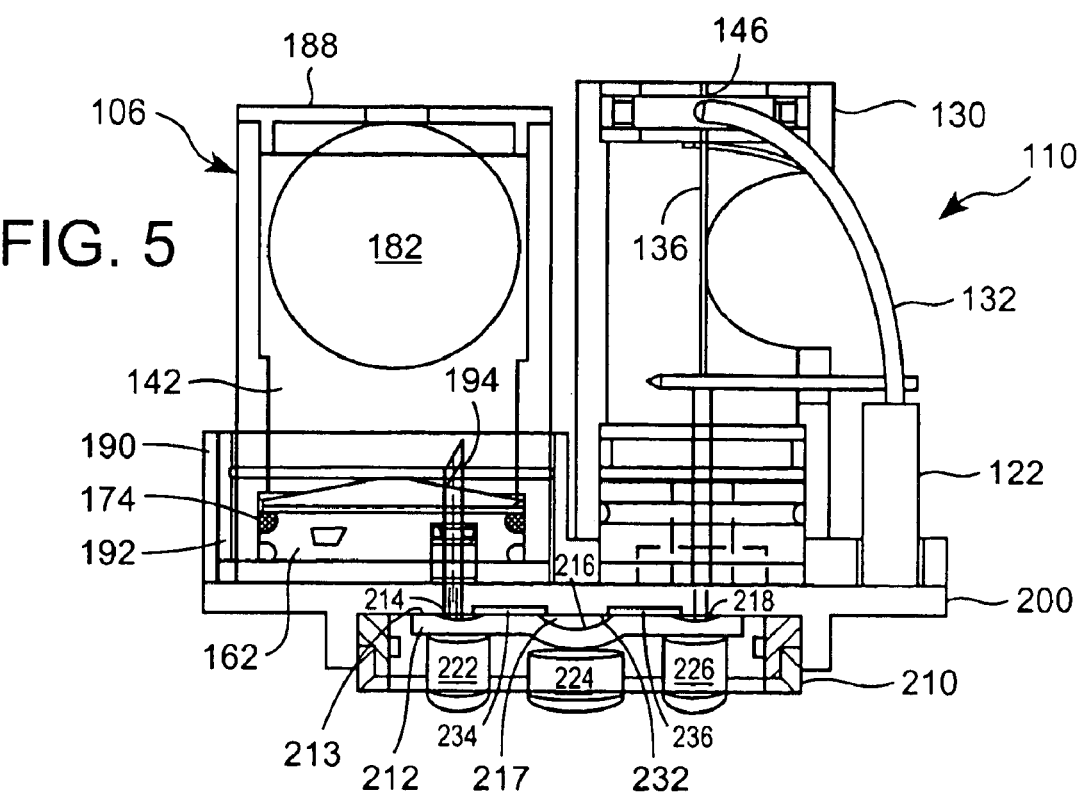
FIG. 5 illustrates the fluid delivery assembly detached from the drive assembly of the aerosol generator of FIG. 4.
Figure 6:
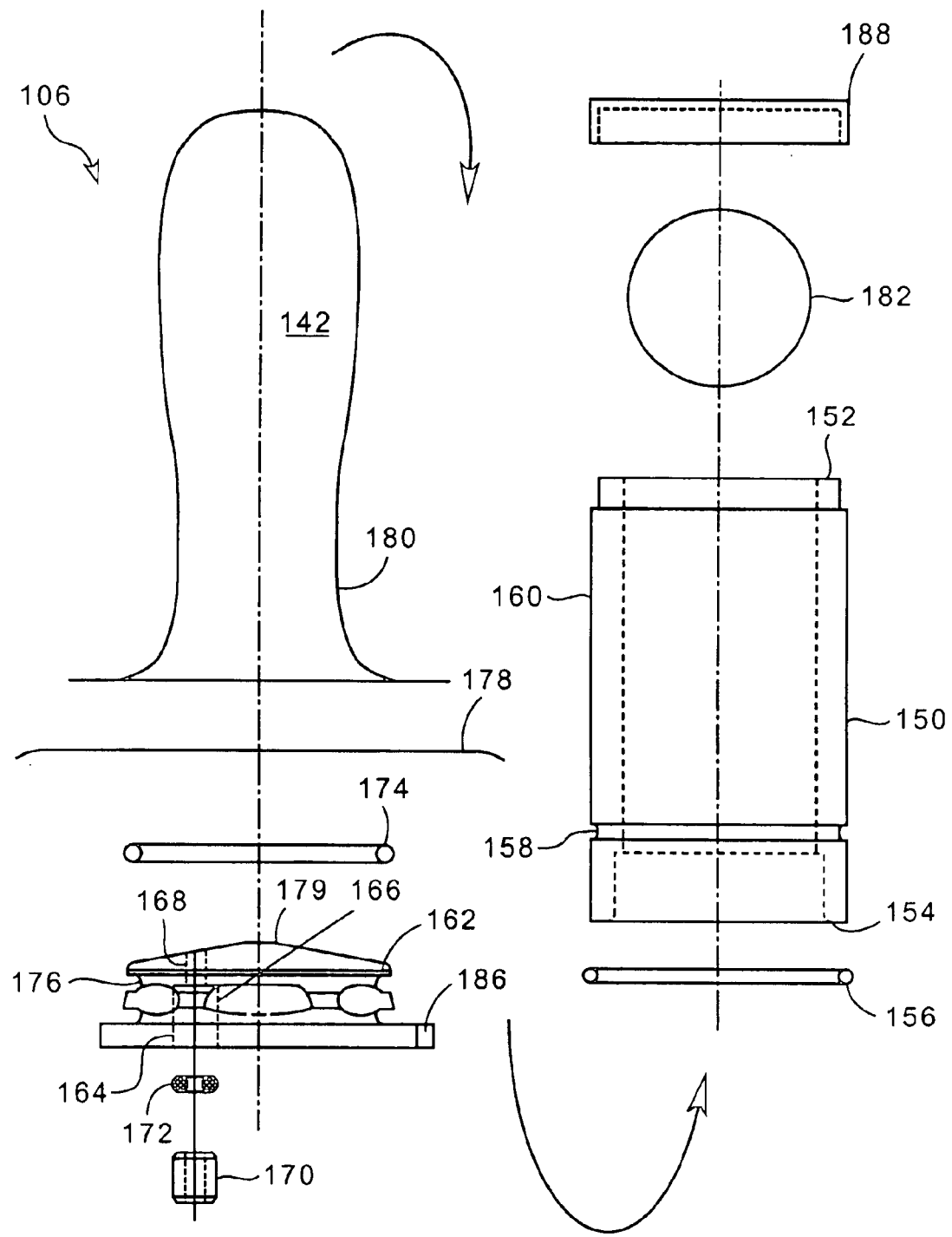
FIG. 6 is an exploded view of an embodiment of a reservoir.
Figure 7:
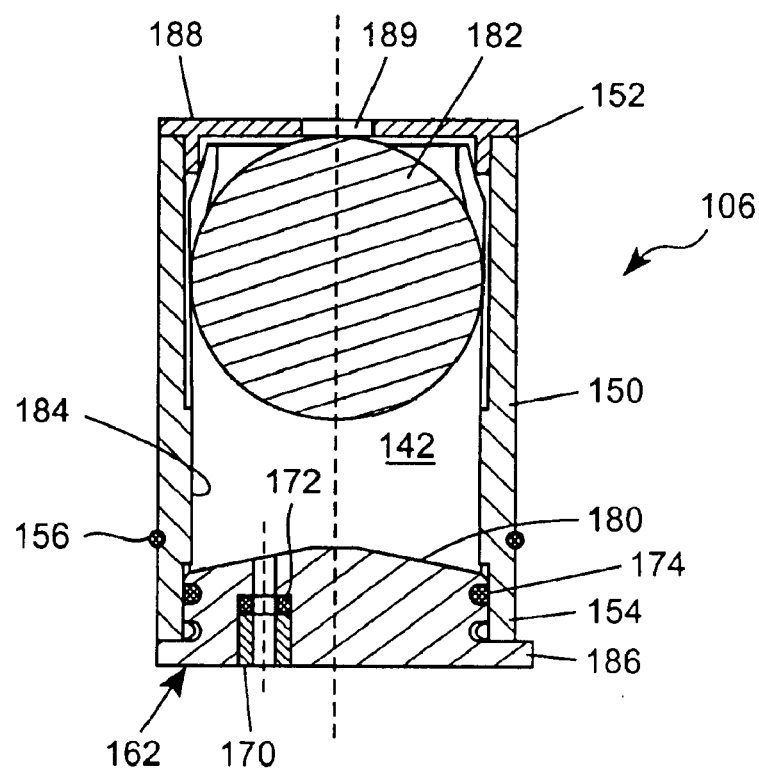
FIG. 7 illustrates the reservoir of FIG. 6 in an assembled condition.

FIG. 4 illustrates the fluid delivery assembly 110 and the drive assembly 112 in an assembled condition. In accordance with a preferred embodiment, the fluid delivery assembly 110 is removably detachable from the drive assembly 112. FIG. 5 shows the fluid delivery assembly 110 detached from the drive assembly.

The fluid delivery assembly 110 and the drive assembly 112 can be removably attached to each other by any suitable attachment construction. For example, the fluid delivery assembly 110 can be attached to the drive assembly 112 by a mechanical connection, such as a snap-fit engagement, or by a twist-on engagement. For example, conductive contacts (not shown) can be provided on the drive assembly 112 to make electrical contact with the heater 130, when the fluid delivery assembly 110 is attached to the drive assembly 112.

In such embodiments of the aerosol generator 100, the fluid delivery assembly 110, which includes the wetted components of the aerosol generator, can be replaced in the aerosol generator as a complete unit. For example, the fluid delivery assembly 110 can be replaced after the medicament contained in reservoir 106 has been consumed. A fluid delivery assembly 110 including a reservoir containing the same or a different medicament can then be installed on the drive assembly of the aerosol generator.

The heater 130 of the fluid delivery assembly 110 includes a capillary sized flow passage 136. The capillary passage 136 can comprise a selected length of metal tubing. For example, the length of the capillary passage can be from 0.5 to 10 cm, and preferably from 1 to 4 cm. In a preferred embodiment, metal tubing comprises a heater which is heated by passing an electrical current along a length of the tubing via a first electrode 138 and a second electrode 140. However, the capillary passage can have other suitable alternative constructions. For example, in an alternative embodiment, the capillary passage can be formed in a polymer, glass, metal and/or ceramic laminate, which includes a heater comprising resistance heating material.

The capillary passage 136 can have any suitable dimensions. For example, the capillary passage can have a maximum width of 0.01 to 10 mm, preferably 0.05 to 1 mm, and more preferably 0.1 to 0.5 mm. Alternatively, the capillary passage can be defined by its transverse cross sectional area, which can be $8 \times 10^{-5}$ to 80 mm$^2$, preferably $2 \times 10^{-3}$ to $8 \times 10^{-1}$ mm$^2$, and more preferably $8 \times 10^{-3}$ to $2 \times 10^{-1}$ mm$^2$. The capillary passage 136 heats medicament 142 supplied from the reservoir 106 during operation of the aerosol generator 100. In accordance with an embodiment, the reservoir 106 has a dose capacity for delivering doses of a selected volume. For example, the doses can be 5 µl doses and the reservoir can be sized to contain preferably from between about 10 doses to about 500 doses, e.g., 50 to 250 doses. However, the dose capacity of the reservoir is not limited and will depend on the desired dose volume, which can be determined by the application of the aerosol generator.

As shown with reference to FIGS. 3–5, the pressure transducer 122 is in fluid communication with the mouthpiece 134 via the air passage 132. The air passage 132 includes the air inlet 124 through which ambient air within the housing is drawn into the air passage 132 by a user inhaling on the mouthpiece 134. In a preferred embodiment, the aerosol generator 100 is activated by a user inhaling on an outlet 144 of the mouthpiece 134. This inhalation causes a differential pressure in the air passage 132, which is sensed by the pressure sensor 122. The pressure sensor 122 can be extremely sensitive. For example, the pressure sensor can be triggered at a selected threshold value of air flow through the air passage 132, for example, as low as about 3 liters/min.

This value equals less than about 1/10 of the typical human inhalation flow rate. Accordingly, the user can trigger the pressure sensor without wasting appreciable lung volume.

In an alternative embodiment of the aerosol generator, the fluid delivery assembly 110 and drive assembly 112 can be activated by a user depressing the switch 128.

The pressure sensor 122 activates the drive assembly 112 and the fluid delivery assembly 110 to cause liquid medicament 142 (e.g., a drug and liquid carrier) to flow from the reservoir 106 to the capillary passage 136 of the heater 130. The capillary passage 136 heats the medicament to a sufficiently high temperature to vaporize the liquid medicament. Ambient air is delivered through the air passage 132 to a region 146 at which the vaporized medicament from the capillary passage 136 is admixed with the ambient air to produce an aerosol.

In alternative embodiments, a pressurized air source can be used with the aerosol generator to provide dilution air to mix with the vaporized medicament. For example, the pressurized air source can be a compressed air source located within the aerosol generator (not shown), a fan/blower to flow air into the mouthpiece, or any other suitable device.

The control electronics 120 can perform various selected functions in the aerosol generator. For example, the control electronics can control the temperature profile of the capillary passage 136 during operation of the aerosol generator 100. The control electronics 120 can also control the display 114. The display is preferably a liquid crystal display (LCD). The display can depict selected information pertaining to the condition or operation of the aerosol generator 100. The control electronics can also control the operation of a motor, such as stepper motor 148 of the drive assembly 112 during operation of the aerosol generator 100; monitor the Hall-effect transducer 108, which is operatively associated with the stepper motor 148 to determine the termination of a cycle of the drive assembly; monitor the initial pressure drop caused by inhalation and sensed by the pressure sensor 122; monitor the condition of the battery unit 116 that provides electrical power to components of the aerosol generator; and monitor the operation of the capillary passage 136.

In the embodiment shown in FIG. 3, the battery unit 116 can be, for example, a rechargeable battery, such as a 6 volt nickel metal hydride (NiMH) battery pack including multiple cells. In this embodiment, the battery unit includes multiple batteries (e.g., Sanyo HF-C1U, 600 mAh NiMH batteries) in series, which provides sufficient energy to operate the aerosol generator for delivery of at least 100 doses of 5 $\mu$l volumes of medicament. The battery unit is preferably rechargeable via the charging jack 118. The battery unit provides power to components of the aerosol generator (e.g., the control electronics 120, pressure transducer 122, etc.) and the master on/off switch.

The master on/off switch controls powering up and powering down of the aerosol generator 100 during operation. The master on/off switch also activates the display 114. In an exemplary embodiment, the display provides information including, for example, the number of doses remaining within the reservoir 106, a failure of the heater 130, and a detected low voltage condition of the battery unit 116.

During operation of the aerosol generator 100, a user removes the cap 104 to activate components of the aerosol generator and expose the mouthpiece 134. The user inhales on the mouthpiece, which creates a pressure drop in the interior of the mouthpiece. This pressure drop is detected by the pressure sensor 122. Upon sensing the pressure drop, the pressure sensor sends a signal to a controller included in the control electronics 120, which operates the fluid delivery assembly 110. Alternatively, a user can press the switch 128 to cause a signal to be sent to the controller, to activate the fluid delivery assembly 110 and the drive assembly 112.

FIGS. 6–8 illustrate an exemplary embodiment of the reservoir 106. The reservoir comprises a body 150 having an open upper end 152 and open lower end 154. The body 150 is preferably tubular shaped. A seal, such as an O-ring 156, fits in a groove 158 formed in the outer surface 160 of the body. A bottom cap 162 includes a through opening 164. The opening 164 includes a first portion 166 and a second portion 168 having a smaller diameter than the first portion. A sleeve 170 and a seal, such as an O-ring 172, fit within the first portion 166 of the opening (FIGS. 7 and 8). The bottom cap 162 also includes an O-ring 174, which fits in an exterior annular groove 176 (FIGS. 7 and 8). The bottom cap includes an upper surface 179, preferably having a domed shape.

The reservoir 106 also comprises a bladder including a lower bladder wall 178 and an upper bladder wall 180. The lower bladder wall 178 and upper bladder wall 180 are preferably sealed together. The bladder is preferably made of a flexible material, such as an elastomer, rubber, or the like. The bladder is sized to hold a selected volume of liquid medicament, typically a certain number of doses of medicament. The bladder containing the liquid medicament is preferably sealed.

The reservoir 106 further comprises a weight 182. FIG. 7 illustrates the reservoir in an assembled condition. As shown, the weight 182 is positioned inside the body 150 above the upper bladder wall 180. The weight exerts a constant force (equal to the mass of the weight, m, multiplied by the gravitational constant, g) on liquid medicament 142 contained within the bladder, when the reservoir is in a vertical orientation, as shown. When the reservoir is in a horizontal orientation (not shown), the weight rests against the inner surface 184 of the body. The weight 182 is spherical shaped; however, the weight can have any other suitable shape. The weight can be made of any suitable material, such as metals, ceramics and/or plastics, having the desired mass to exert the desired pressure on the liquid in the bladder. As shown, the weight 182 preferably is sized to fit closely within the body, so that the weight is constrained to move slidably in a rectilinear path in the reservoir chamber, to ensure maximum contact between the weight and the upper bladder wall in the vertical orientation of the reservoir, so as maintain substantially constant pressure on the liquid.

In the assembled condition shown in FIG. 7, the bottom cap 162 is attached at the lower end 154 of the body 150. The bottom cap 162 includes a protrusion 186 (see also FIG. 6), which extends radially outward beyond the outer surface of the body. The O-ring 174 forms a seal between the bottom cap 162 and the inner surface 184 of the body. An upper cap 188 is removably or permanently attached at the upper end 152 of the body 150, such as by a snap-fit engagement, adhesive bonding, or the like. The upper cap 188 preferably includes an opening such that the interior of the reservoir is open to the atmosphere.

FIGS. 4 and 5 show the reservoir 106 mounted to a receptacle 190 of the fluid delivery assembly 110. To mount the reservoir 106 to the receptacle 190, the lower end of the body 150 is placed inside the receptacle such that the protrusion 186 of the bottom cap 162 is received in a slot 192 formed in the receptacle. The receptacle 190 also includes an upstanding flow conduit 194. The flow conduit is preferably a hollow tube having a sharp tip 196. The protrusion 186 and mating slot 192 are designed to ensure that when the reservoir is mounted to the receptacle, the flow conduit 194 is received in the opening 164 in the bottom cap 162, such that the pointed tip is positioned above the upper surface 179. When the reservoir is fully received in the receptacle, the O-ring 156 forms a seal between the outer surface of body 150 of the reservoir and the inner surface of the receptacle (FIG. 5). The reservoir and receptacle can include engagement elements (not shown) to provide mechanical engagement of the reservoir in the receptacle. Alternatively, the reservoir can be retained in the receptacle by a frictional engagement, or the like.

Figure 8:
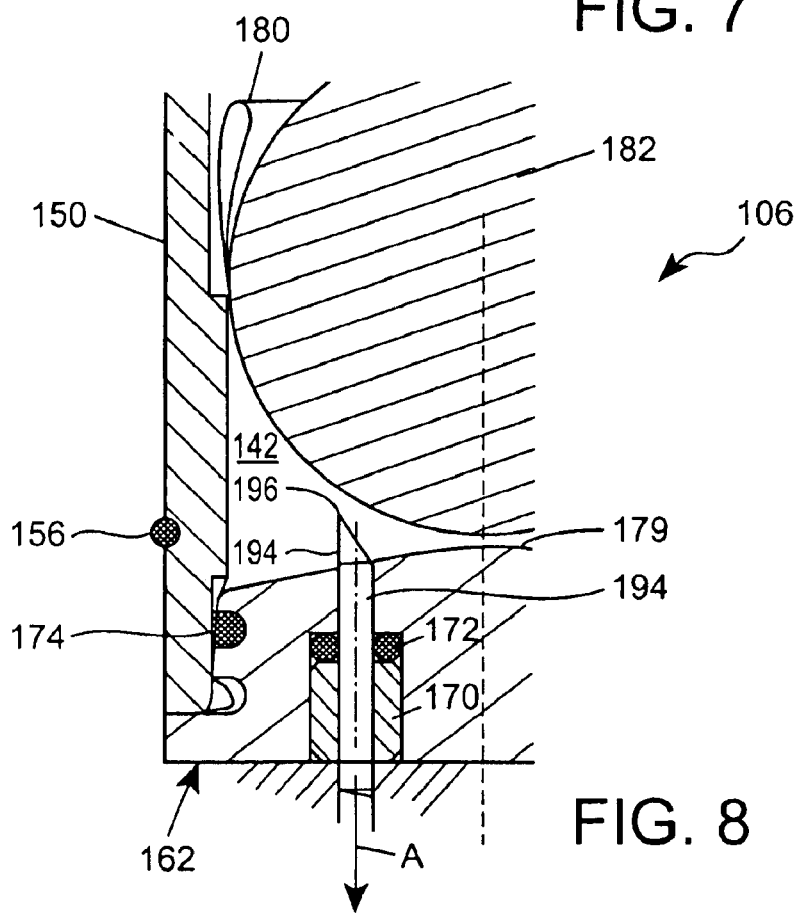
FIG. 8 is an enlarged partial view of the reservoir of FIG. 7 after the upper bladder portion has been pierced by a flow conduit in accordance with an embodiment.

During mounting of the reservoir 106 to the receptacle, the tip 196 of the flow conduit 194 penetrates the lower bladder wall 178 as depicted in FIG. 8. The domed shape of the upper surface 179 of the bottom cap 162 shapes the lower bladder wall such that it can be more easily perforated by the tip 196. In addition, the domed shape ensures that the weight 182 does not contact the tip 196 during insertion of the reservoir on the receptacle, or later as liquid is dispensed from the bladder. When the lower bladder wall 178 is pierced by the tip 196, the liquid medicament 142 can flow from the bladder into the flow passage, as indicated by arrow A in FIG. 8. The force applied to the medicament in the reservoir by the weight 182 maintains flow of the medicament into the flow passage.

Figure 9:
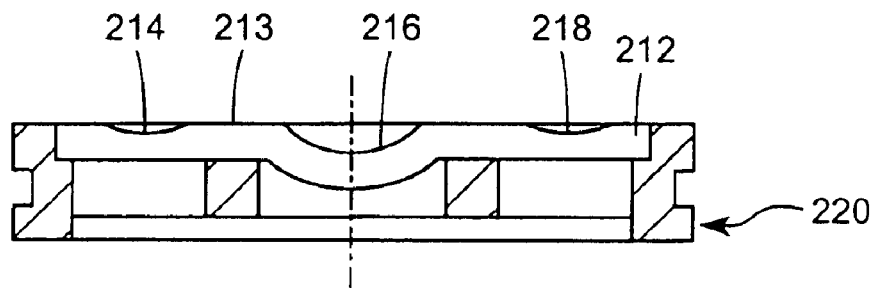
FIG. 9 illustrates a carrier including an elastomeric member in accordance with an embodiment.

With reference to FIGS. 4 and 5, in a preferred embodiment of the fluid delivery assembly 110, the flow passage for the medicament is defined between an upper member 200 and a lower member 210. The lower member 210 includes an elastomeric member 212 made of a material capable of being repeatedly deformed and then returning to its original shape. The elastomeric member 212 includes an upper surface 213 (FIGS. 9–11) defining concavities or depressions, including an inlet depression 214, a metering depression 216 and an outlet depression 218. The inlet depression 214, metering depression 216 and outlet depression 218 are preferably substantially dome shaped, as shown. The metering depression 216 has a selected volume so that it can contain a predetermined volume of the medicament 142. The inlet depression 214 acts as an inlet valve, the outlet depression 218 acts as an outlet valve, and the metering depression 216 acts as a metering chamber, in the flow passage, as described in greater detail below. As shown in FIG. 9, the elastomeric member 212 can be supported by a carrier 220, such as a molded piece of plastic.

Figure 10:
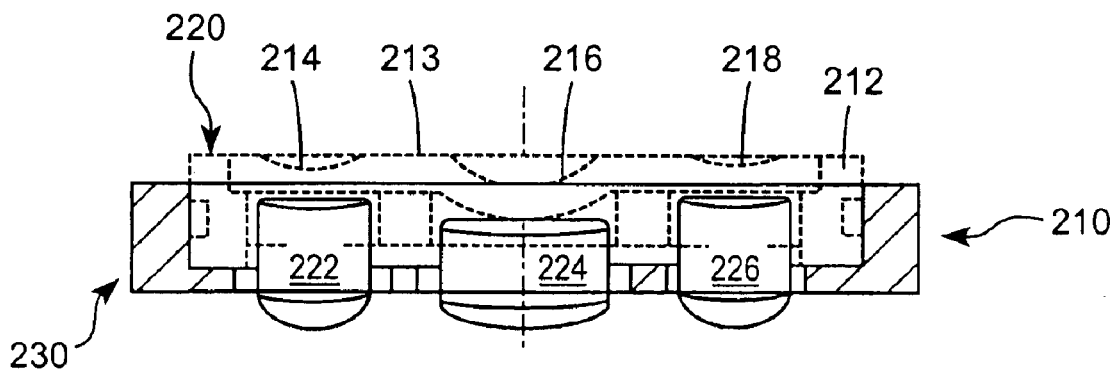
FIG. 10 illustrates the carrier of FIG. 9 in broken line mounted to an actuator carrier in accordance with an embodiment.
Figure 11:
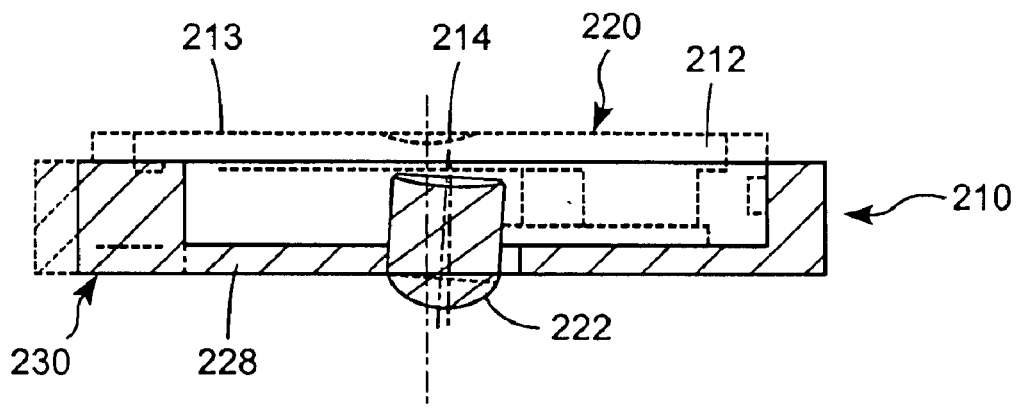
FIG. 11 shows a portion of the carrier of FIG. 9 in broken line and a resiliently biased actuator of the actuator carrier in accordance with an embodiment.

With reference to FIGS. 9–11, the lower member 210 also includes an inlet actuator 222, dispensing actuator 224 and outlet actuator 226, which are operatively associated with the inlet depression 214, dispensing depression 216 and outlet depression 218, respectively, of the elastomeric member 212. The inlet actuator 222, dispensing actuator 224 and outlet actuator 226 are preferably provided on movable arms, such as flexible or resilient portions of lower member 210 (only arm 228 associated with inlet actuator 222 is shown in FIG. 11). As shown in FIG. 11, the actuators and arms can be formed integrally with an actuator carrier 230 from metal or plastic material. As shown in FIG. 10, the inlet actuator 222, dispensing actuator 224 and outlet actuator 226 can be provided in the actuator carrier 230, which is removably attachable to the carrier 220 including the inlet depression 214, metering depression 216 and outlet depression 218, e.g., the carrier 220 can be received in a recess.

The construction of the lower member 210 shown in FIGS. 9–11 provides increased versatility in the aerosol generator. Namely, this construction enables the use of replaceable carriers 220 having different sized metering volumes, while a common actuator carrier 230 can be used with different carrier 220 constructions. Accordingly, such embodiments enable different medicament doses to be delivered, depending on the desired application of the aerosol generator. If desired, such constructions can be manufactured by techniques, such as injection molding, which can simplify manufacturing. In addition, the carrier 220 and actuator carrier 230 can be formed in round shapes, which can provide good seals, as well as reduce manufacturing costs, as compared to more complex shapes.

The upper member 200 can be made of any suitable metal, polymer, ceramic or glass material, which is more rigid than the material forming the elastomeric member 212 of the lower member 210. The upper member 200 has a lower surface 232 (FIG. 5), which defines flow passages 234, 236. As shown in FIG. 5, when the lower member 210 is attached to the upper member 200, the flow passage 234 partially overlaps the inlet depression 214 and metering depression 216, and the flow passage 236 partially overlaps the metering depression 216 and the outlet depression 218. The flow passage 234 allows fluid flow between the inlet depression 214 and the metering depression 216, and the flow passage 236 allows fluid flow between the metering depression 216 and the outlet depression 218, as described in greater detail below.

Referring to FIG. 4, an exemplary embodiment of the drive assembly 112 of the aerosol generator 100 comprises the stepper motor 148; a gear 240 driven by the stepper motor 148; and a camshaft 242 including camshaft lobes 244, 246 and 248, and a gear 250, which engages with the gear 240. When the stepper motor 148 rotates the gear 240, the camshaft 242 also rotates due to the engagement of the gears 240 and 250. As the camshaft 242 rotates, camshaft lobes 244, 246 and 248 also rotate. During this rotation, the camshaft lobes 244, 246 and 248 operatively couple with the inlet actuator 222, dispensing actuator 224 and outlet actuator 226, respectively.

During rotation, the camshaft lobes 244, 246 and 248 activate the inlet actuator 222, dispensing actuator 224 and outlet actuator 226, respectively, in a desired sequence determined by the configuration of the camshaft lobes. For example, the camshaft lobe 244 operatively couples with the inlet actuator 222, thereby opening and closing the flow passage by acting on the inlet depression 214 during rotation of the camshaft 242. The camshaft lobe 246 operatively couples with the dispensing actuator 224 to cause the metering chamber 217 defined by the metering depression 216 to be emptied during rotation of the camshaft 242 by acting on the metering depression 216. Preferably, fluid is ejected out of the metering chamber 217 at a substantially constant flow rate. The camshaft lobe 248 operatively couples with the outlet actuator 226, which opens and closes the flow passage by acting on the outlet depression 218. Thus, the camshaft lobe 244 cooperates with the inlet actuator 222 and metering depression 214 to form an inlet valve, and camshaft lobe 248 cooperates with the outlet actuator 226 and outlet depression 218 to form an outlet valve.

As described above, when the cap 104 is removed and a user inhales on the mouthpiece 134, the pressure drop in the mouthpiece 144 is sensed by the pressure sensor 122. Upon detection of the pressure drop by the pressure sensor 122, the pressure sensor 122 sends a signal to the control circuitry 120, which causes activation of the stepper motor 148. Alternatively, the stepper motor 148 can be activated by a user pressing the switch 128. In an embodiment, the stepper motor 148 can be any suitable stepper motor that can controllably drive the camshaft 242 a precise amount (e.g., one revolution). For example, the stepper motor may be obtained from MicroMo Electronics, Inc. located in Clearwater, Fla.

Figure 12:
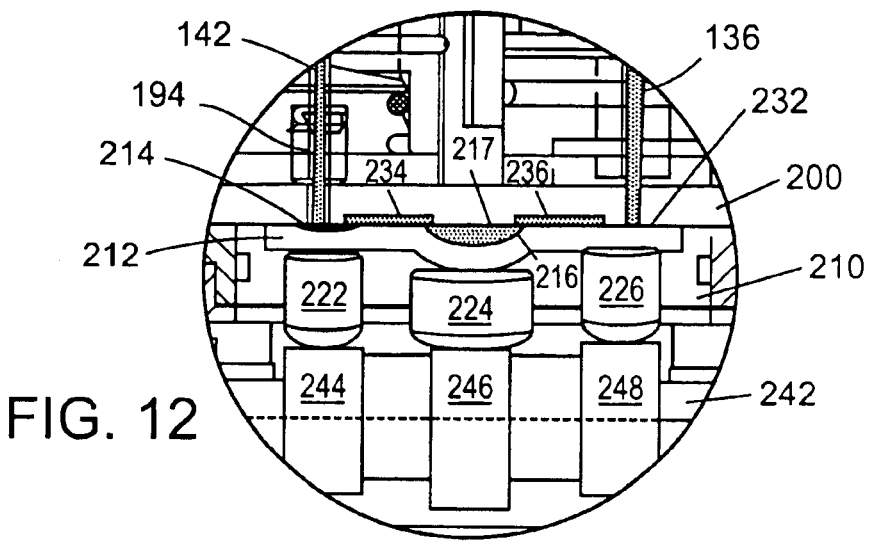
FIG. 12 is an enlarged partial schematic view of the fluid delivery assembly shown with reference to FIGS. 4 and 5, in which the fluid delivery assembly is in a filling cycle in accordance with an embodiment.
Figure 13:
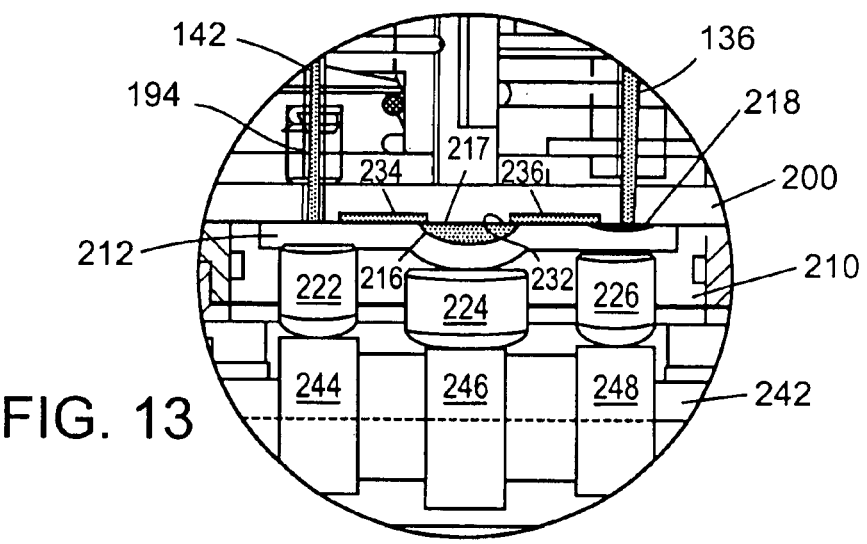
FIG. 13 an enlarged partial schematic view of the fluid delivery assembly shown in FIG. 12, in which the dispensing chamber is filled in accordance with an embodiment.
Figure 14:
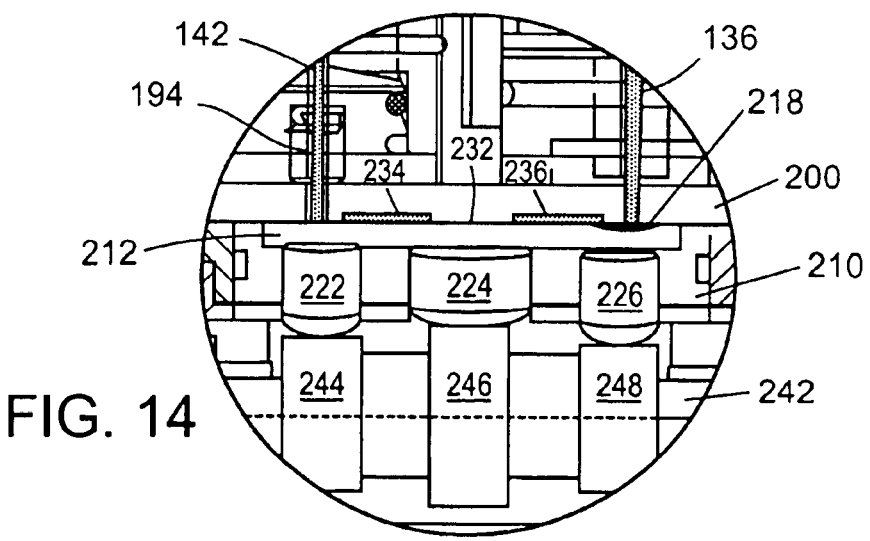
FIG. 14 an enlarged partial schematic view of the fluid delivery assembly shown in FIG. 12 in which the dispensing chamber has been emptied in accordance with an embodiment.

Referring to FIGS. 12–14, the metering chamber 217 is emptied by moving the dispensing actuator 224. For instance, when the camshaft lobe 246 engages with the dispensing actuator 224, an upper surface of the dispensing actuator 224 presses against the elastomeric member 212 and at least partially compresses the metering depression 216. FIG. 14 shows the metering depression 216 fully depressed by the dispensing actuator 224, such that the elastomeric member is pressed against the opposing surface 232 of the upper member 200. The upward movement of the metering depression 216 forces fluid in the metering chamber 217 into the flow passage 236, while fluid in the flow passage 236 is forced into the capillary passage 136. The elastomeric member 212 preferably forms a seal at the locations of the inlet depression 214 (inlet valve) and outlet depression 218 (outlet valve) such that the inlet valve and outlet valve can be opened or closed when the inlet actuator 222 and outlet actuator 226, respectively, act on the inlet depression 214 and outlet depression 218. The metering chamber 217 ensures that a desired amount of the medicament 142 is delivered by the aerosol generator 100 to the user. The metering chamber can have a selected volume (e.g., 5 μl). However, the metering depression can be sized so that the metering chamber 217 has any desired volume depending upon the application of the aerosol generator 100. After delivery of the selected volume of the medicament to the capillary passage 136, the outlet valve is closed by engagement of camshaft lobe 248 with the outlet actuator 226, which depresses the outlet depression 218.

FIG. 12 illustrates the fluid delivery assembly 110 during a fill cycle wherein the metering chamber 217 is filled with medicament 142 from the reservoir. During the fill cycle, the camshaft 242 is rotated such that the camshaft lobe 244 opens the inlet valve at the inlet depression 214 and the camshaft lobe 248 closes the outlet valve at the outlet depression 218, while maintaining the dispensing actuator 224 in a position that allows the medicament 142 to fill the metering chamber 217.

FIGS. 13 and 14 schematically illustrate the fluid delivery assembly 110 during delivery of the aerosol. During this operation, the camshaft lobe 244 closes the inlet valve by compressing the inlet depression 214. As the inlet valve closes, the camshaft lobe 248 opens the outlet valve at the location of the outlet depression 218, while the camshaft lobe 246 presses the dispensing actuator 224 against the metering depression 216 to force fluid through the fluid passage 236 and into the heated capillary passage 136.

FIG. 14 schematically illustrates the fluid delivery assembly 110 at the end of the aerosol delivery cycle. As shown, the camshaft lobe 246 has moved the dispensing actuator 224 into a fully dispensed position in which the dispensing actuator 224 presses the elastomeric member 212 against the opposed surface 232 to thereby empty the metering chamber 217.

The medicament 142 flows through the heated capillary passage 136 and exits as a vaporized fluid. At the exit of the capillary passage 136, ambient air provided via the air passage 132 admixes with the vaporized fluid in the region 146 (FIG. 4). Consequently, aerosol can be supplied to the patient early in the patient's inhalation breath cycle to thereby deliver a precise dose of medication to the lungs of the patient.

Figure 15:
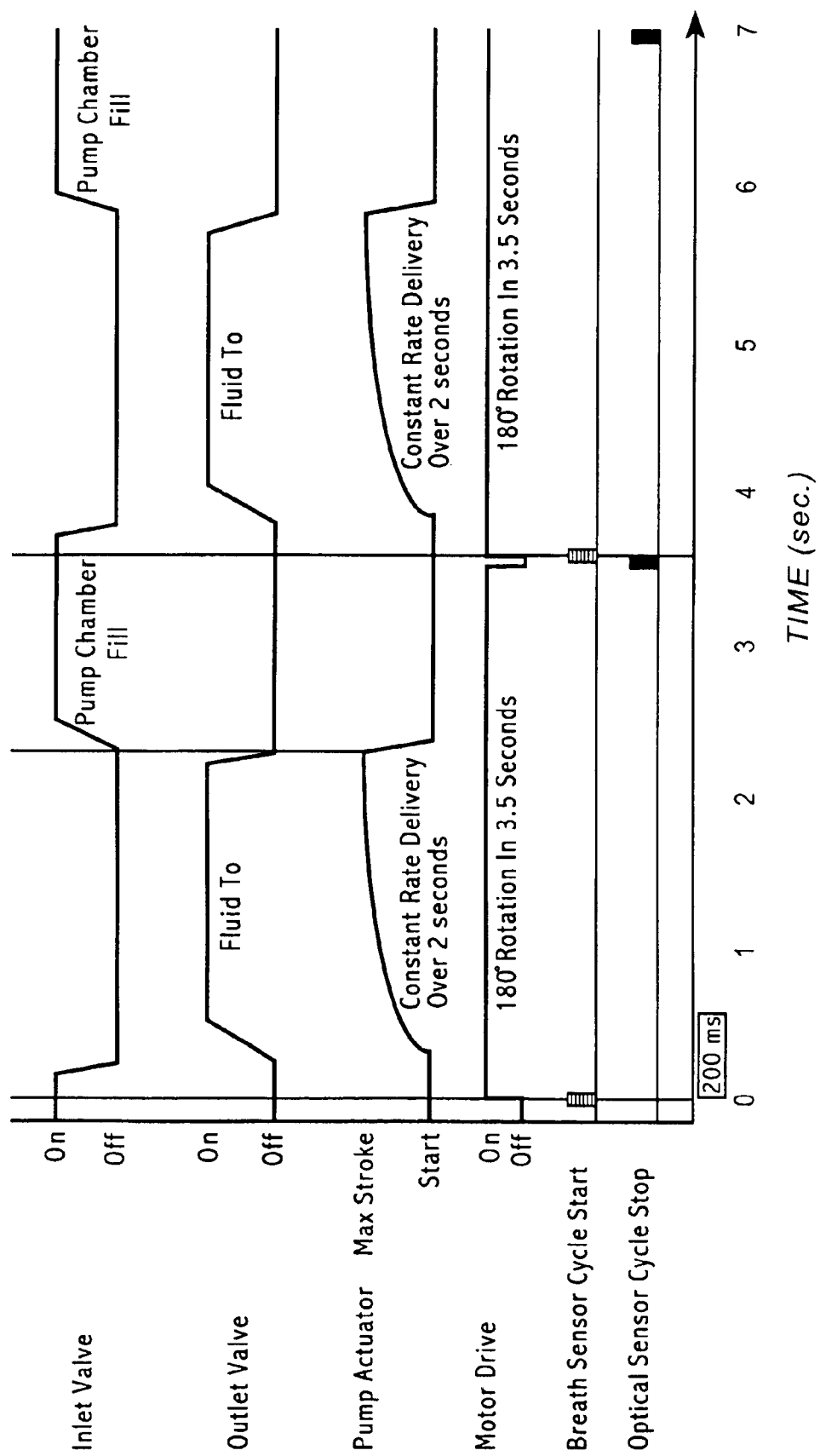
FIG. 15 is a schematic of a timed sequence of operation of the aerosol generator in accordance with an embodiment.

FIG. 15 illustrates a time sequence of the inlet valve, the outlet valve, the dispensing actuator (pump actuator), the stepper motor, the pressure sensor (breath sensor) and the Hall-effect transducer coupled to the stepper motor. As shown, within 200 milliseconds of detecting a user inhaling on the mouthpiece, the inlet valve is closed (i.e., the inlet depression 214 is compressed by the inlet actuator 222) and then the outlet valve is opened (i.e., the outlet depression 218 is maintained in an open position by the outlet actuator 226). Ambient air is drawn into the mouthpiece by the patient inhaling through the outlet of the mouthpiece. With the outlet 144 valve open, the dispensing actuator provides a constant rate of delivery of a precise volume of fluid to the heated capillary passage over a predetermined time period, e.g., a 2 second period. The ambient air admixes with the vapor exiting the heated capillary passage to form an aerosol and the patient inhales the aerosol. Subsequently, the outlet valve is closed and then the inlet valve is opened to refill the metering chamber. Because the aerosol is delivered at the beginning of the patient's breath inhalation, the drug formulation in the aerosol can be effectively administered.

Figure 16:
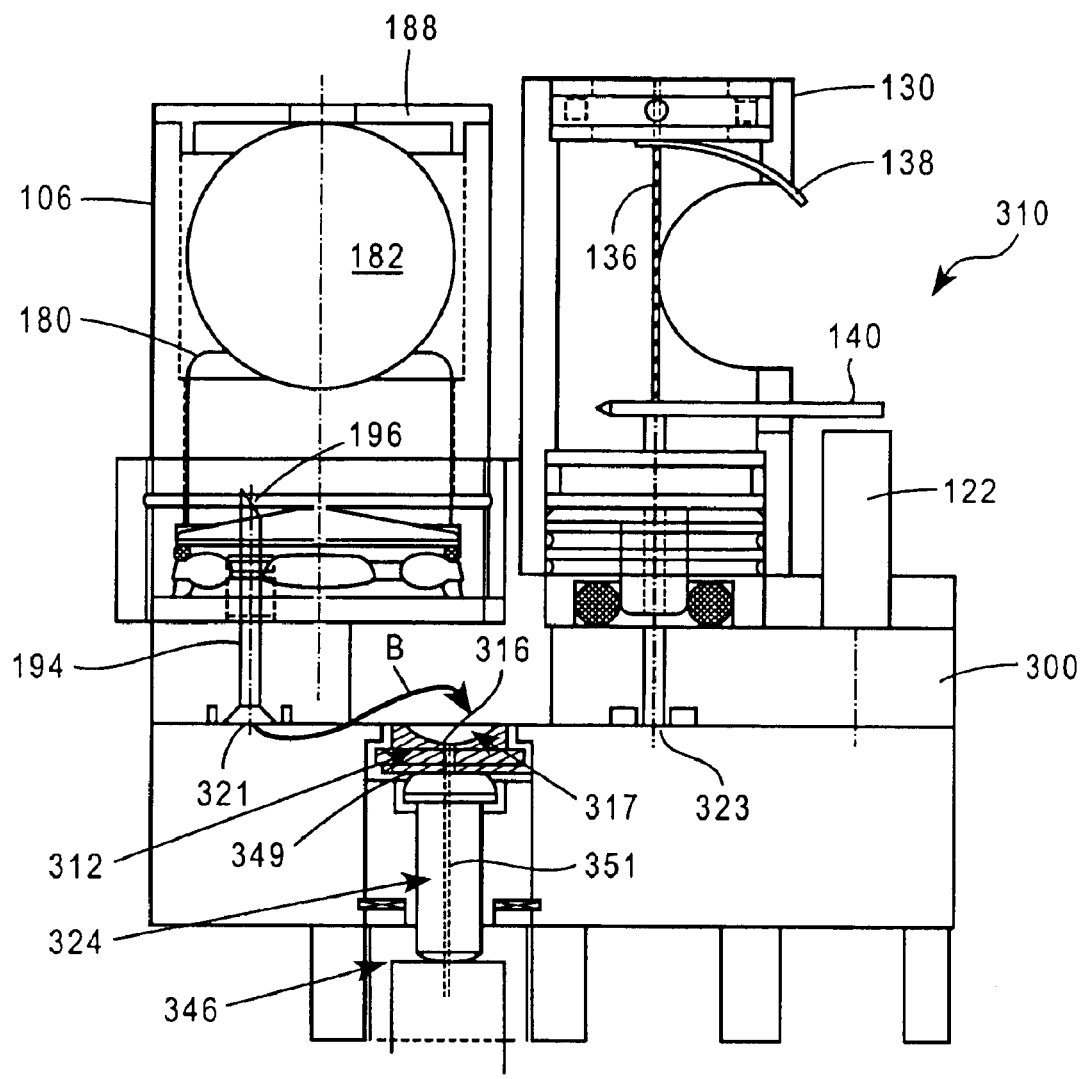
FIG. 16 illustrates a fluid delivery assembly in accordance with an embodiment, in which the dispensing chamber is filled.
Figure 17:
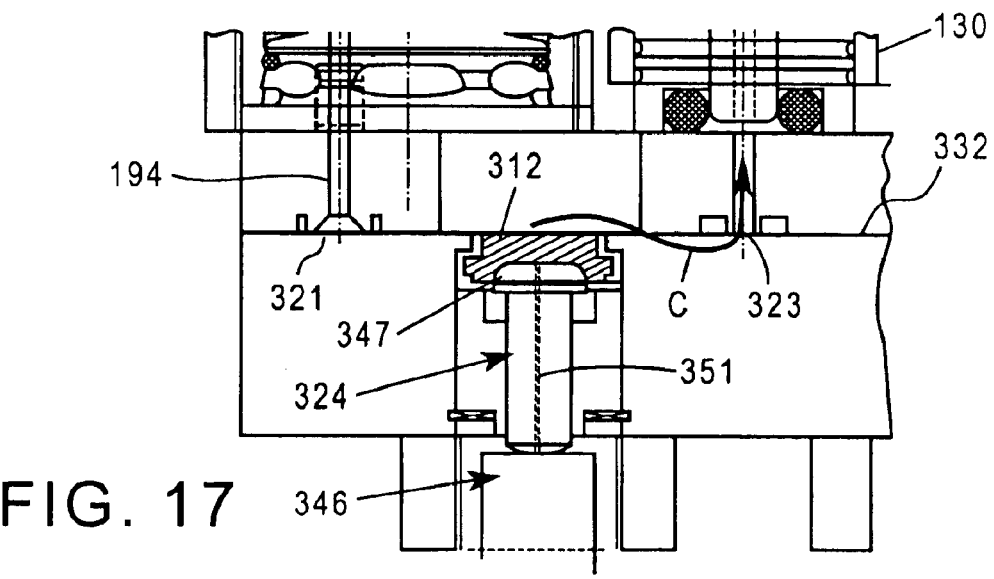
FIG. 17 is a partial view of the fluid delivery assembly of FIG. 16, in which the dispensing chamber is emptied.
Figure 18:
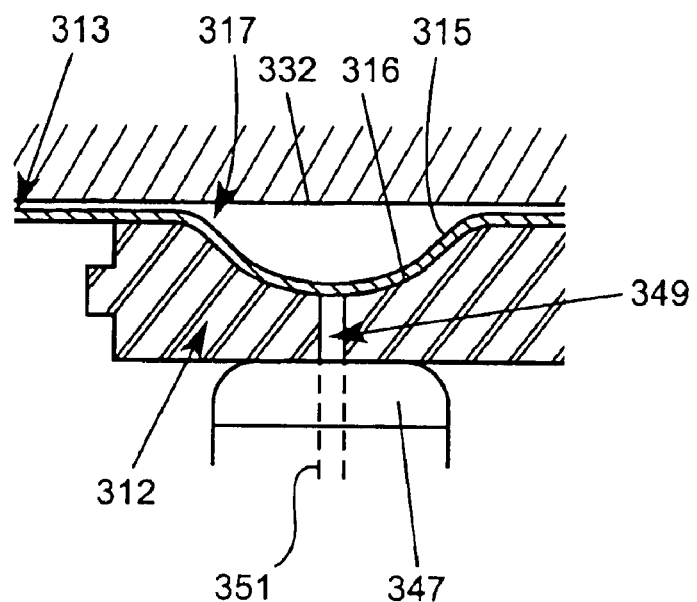
FIG. 18 is an enlarged partial view of the fluid delivery assembly of FIG. 16, showing the elastic membrane.

FIGS. 16–18 illustrate an alternative embodiment of the fluid delivery assembly 310 (the air passage is not shown). In this embodiment, the elastomeric member 312 includes a metering depression 316 operatively associated with a metering actuator 324. As shown in FIG. 18, the elastomeric member 312 also includes an elastomeric membrane 313, which extends upstream between the metering chamber 317 and an inlet valve 321, and extends downstream between the metering chamber 317 and an outlet valve 323. The elastomeric membrane 313 forms a lower wall of the flow passage. The elastomeric member 312 has a vent 349, which facilitates the unrestricted filling of the metering depression 316 by allowing trapped air between the actuator 324 and the elastic membrane 313 to escape.

The metering actuator 324 is operatively associated with cam lobe 346 and has a head 347, which contacts the elastomeric member 312. The metering actuator 324 is operable to depress the metering depression 316, to effect emptying of the metering chamber 317 during dispensing of the aerosol. When the metering depression 316 is in a position as shown in FIG. 16, liquid can fill the metering chamber from the reservoir 106 as indicated by arrow B. When the metering depression 316 is placed in a position as shown in FIG. 17 by upward movement of the actuator 324, liquid is emptied from the metering chamber and flows into the capillary passage 136 as indicated by arrow C. The head 347 also includes an air vent slot 351 that allows venting to occur regardless of the actuator orientation.

Figure 19:
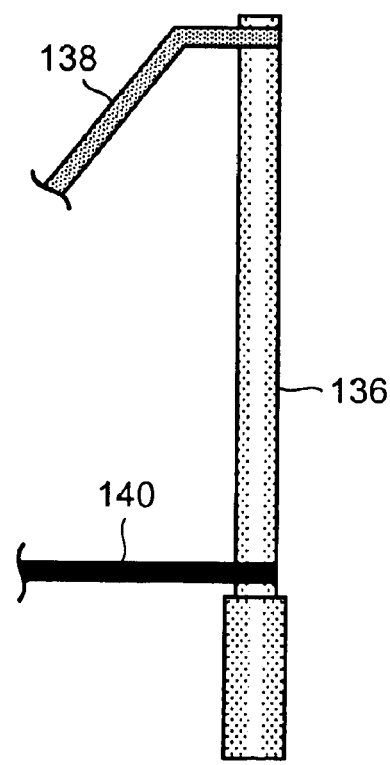
FIG. 19 illustrates a capillary with two electrodes in accordance with an embodiment.

FIG. 19 shows an embodiment of a preferred heater arrangement in which the capillary passage 136 comprises an electrically conductive tube provided with the electrode 138, which is the downstream electrode, and the electrode 140, which is the upstream electrode. In this embodiment, the capillary passage 136 is a controlled temperature profile design such as disclosed in copending and commonly assigned application Ser. No. 09/957,026, filed Sep. 21, 2001, which is incorporated herein by reference in its entirety. In the controlled temperature profile capillary, the electrode 138 has an electrical resistance sufficient to cause it to be heated during operation of the aerosol generator, thereby minimizing heat loss at the outlet end of the capillary tube.

In the case where the capillary passage is formed from a tube, the tube can be made of any suitable material. For example, the tube can be made entirely of stainless steel or any other suitable electrically conductive materials.

Alternatively, the tube can be made of a non-conductive or semi-conductive tube incorporating a heater formed from an electrically conductive material, such as platinum. Two electrodes are connected at spaced positions along the length of the tube or heater such that a heated section is defined between the two electrodes. A voltage applied between the two electrodes generates heat in the heated section of the capillary passage based on the resistivity of the material(s) making up the tube or heater, and other parameters such as the cross-sectional area and length of the heated section. As the fluid flows through the capillary passage into the heated section between the first and second electrodes, the fluid is heated and converted to a vapor. The vapor passes from the heated section of the capillary passage and exits from the outlet. If the volatilized fluid is entrained in ambient air as the volatilized fluid exits from the outlet, the volatilized fluid condenses into small droplets, thereby forming an aerosol. In a preferred embodiment, the MMAD of the droplet size is 0.5 to 2.5 μm.

The temperature of the liquid in the capillary flow passage can be calculated based on the measured or calculated resistance of the heating element. In an exemplary embodiment, the heater is a portion of a metal tube, or alternatively is a strip or coil of resistance heating material. The controller preferably regulates the temperature of the flow passage by monitoring the resistance of the heater.

Resistance control can be based on the simple principle that the resistance of the heater increases as its temperature increases. As power is applied to the heating element, its temperature increases because of resistive heating and the actual resistance of the heater also increases. When the power is turned off, the temperature of the heater decreases and correspondingly its resistance decreases. Thus, by monitoring a parameter of the heater (e.g., voltage across the heater using known current to calculate resistance) and controlling application of power, the controller can maintain the heater at a temperature that corresponds to a specified resistance target. The use of one or more resistive elements could also be used to monitor temperature of the heated liquid in cases where a resistance heater is not used to heat the liquid in the flow passage.

The resistance target is selected to correspond to a temperature that is sufficient to cause heat transfer to the liquid material such that liquid is volatilized and expands out the open end of the capillary passage. The control electronics effect closing of the switch, which activates the heating, thereby applying for a duration of time, energy to the heater and after and/or during such duration, determines the real time resistance of the heater, using input from the measuring device. In this embodiment, the resistance of the heater is calculated by measuring the voltage across a shunt resistor (not shown) in series with the heater (to thereby determine current flowing to the heater) and measuring the voltage drop across the heater (to thereby determine resistance based on the measured voltage and current flowing through the shunt resistor). To obtain continuous measurement, a small amount of current can be continually passed through the shunt resistor and heater for purposes of making the resistance calculation and pulses of higher current can be used to effect heating of the heater to the desired temperature.

If desired, the heater resistance can be derived from a measurement of current passing through the heater, or by other techniques used to obtain the same information. The control electronics then makes decisions as to whether or not to send an additional duration of energy based on the difference between desired resistance target for the heater and the actual resistance as determined by a controller.

In a developmental model, the duration of power supplied to the heater was set at 1 msec. If the monitored resistance of the heater minus an adjustment value is less than the resistance target, the controller is programmed to supply another duration of energy by leaving the switch in the closed ("on") position. The adjustment value takes into account factors, such as, for example, heat loss of the heater when not activated, the error of the measuring device and the cyclic period of the controller and switching device. In effect, because the resistance of the heater varies as a function of its temperature, resistance control can be used to achieve temperature control.

In accordance with an exemplary embodiment, the capillary passage 136 is constructed of 32 gauge, 304 stainless steel tubing having a fluid heating section length of 12 mm. In addition, in this embodiment, the downstream electrode 138 is a 3.5 mm length of 29 gauge tubing while the upstream electrode 140 may have any geometry that minimizes the resistance of the electrode 140, such as gold (Au) plated copper (Cu) pins.

The control electronics 120 can control the temperature of the capillary passage 136 by monitoring the resistance of the heater used to heat the heated capillary passage 136. To illustrate operation of the aerosol generator, a target temperature for the capillary passage 136 can be about 220° C. for purposes of vaporizing propylene glycol (PG). In this embodiment, the measured electrical resistance of the heated capillary passage 136 is preferably 0.4 ohms for a target temperature of about 220° C. In order to achieve a resistance of 0.4 ohms, the control electronics pulses power to the electrode 138. In an exemplary embodiment, the control electronics 120 measures voltage and current in order to calculate the resistance across a length of the capillary tube 136. If the control electronics determines that the resultant resistance is below the target value, the control electronics turns power on for a selected period of time, e.g., 1 ms. The control electronics continues to repeat this process until the target resistance for the capillary passage 136 is achieved. Likewise, if the control electronics determines that the resistance is higher than required for the temperature of the capillary passage 136, the control electronics turns off power for a selected period of time, e.g., 1 ms.

In this embodiment, the control electronics 120 may include any processor capable of controlling the resistance of the capillary tube 136 via the electrodes 138 and 140, such as a microchip PIC16F877, available from Microchip Technology Inc., located in Chandler, Ariz., which is programmed in assembly language. The control electronics includes functionality for controlling both the stepper motor 148, the pressure sensor 122 and the Hall-effect transducer 108, and checking the status of both the battery unit 116 and the display 114 incorporated into the master on/off switch. The control electronics 120 can also include functionality via the processor for displaying the number of remaining doses, information on patient compliance, lockout times and/or child safety locks. After vaporization of the medicament 142 within the capillary passage 136, the vaporized medicament expands into the region 146 and admixes with the ambient air supplied via the air inlet 124.

The aerosol generator can produce aerosols with high number concentrations and also with particle sizes within a selected size range, preferably between about 0.5 μm and about 2.5 μm. The aerosol generator can be constructed in various shapes and sizes, and can be miniaturized to a hand-held, portable device with considerable potential for the targeted delivery of drugs to the deep lung. These aerosols offer a number of advantages for delivering drugs to the deep lung. For example, mouth and throat deposition are minimized while deposition in the deep lung is maximized, especially when combined with a breath hold. Moreover, when using an appropriate hydrophilic carrier, deposition may be further enhanced by hygroscopic growth.

The median particle size of the aerosol can be increased by increasing the capillary size and/or decreasing the fluid flow rate through the capillary passage. The aerosol generator preferably generates aerosols in which 95% of the aerosol particles (aerosol droplets) are smaller than 5.6 µm, and more preferably in the range between about 0.5 µm to about 2.5 µm. The aerosol generator preferably incorporates a processor chip for controlling the generation process. The processor, with suitable sensors, also triggers the aerosol generation at any desired time during an inhalation. The processor may also store and report compliance information for patient feed back. During use of the aerosol generator, the drug to be aerosolized is dissolved in a carrier. By the appropriate choice of hydrophilic carriers, this aerosol generator can take advantage of hygroscopic growth in the respiratory system.

Operation of the preferred aerosol generator is as follows. First, a fluid carrier is pumped through the heated capillary passage along with a drug. The fluid vaporizes in the passage and exits as a vapor jet from the open end of the passage. The vapor jet entrains and mixes with ambient air, cools and then condenses to form a highly concentrated, fine aerosol. The heated passage can take a variety of forms, including the use of a glass capillary wrapped by a heater and a capillary formed from stainless steel. As described above, the application of heat to vaporize the aerosol liquid is typically achieved by resistive heating from passing an electric current through the metal capillary. The applied power is adjusted to maximize the conversion of the fluid into an aerosol.

The aerosol generator can generate aerosols over a range of fluid flow rates dependent on the size of the capillary and the power available to vaporize the fluid. A fluid that may be used to demonstrate aerosol generation for drug delivery is propylene glycol (PG) obtained as USP grade (CAS # 57-55-6) from Fisher Scientific in Atlanta, Ga. The boiling point of PG is 189° C. and it has a density of 1.036 g/mL. Solute compounds used as models for drugs were triphenylmethane (CAS # 519-73-3) and oleyl alcohol (CAS #143-28-2) also available from Fisher Scientific in Atlanta, Ga.

Figure 20:
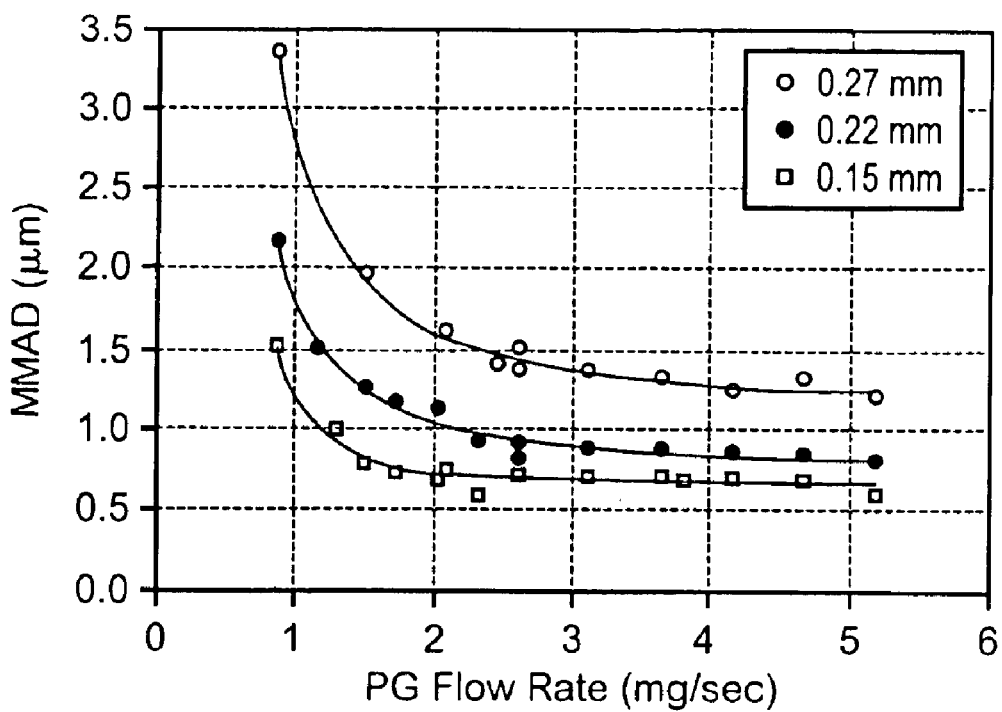
FIG. 20 is a graph illustrating the effect of capillary diameter and mass flow rate on particle size for a propylene glycol aerosol in accordance with an embodiment.
Figure 21:
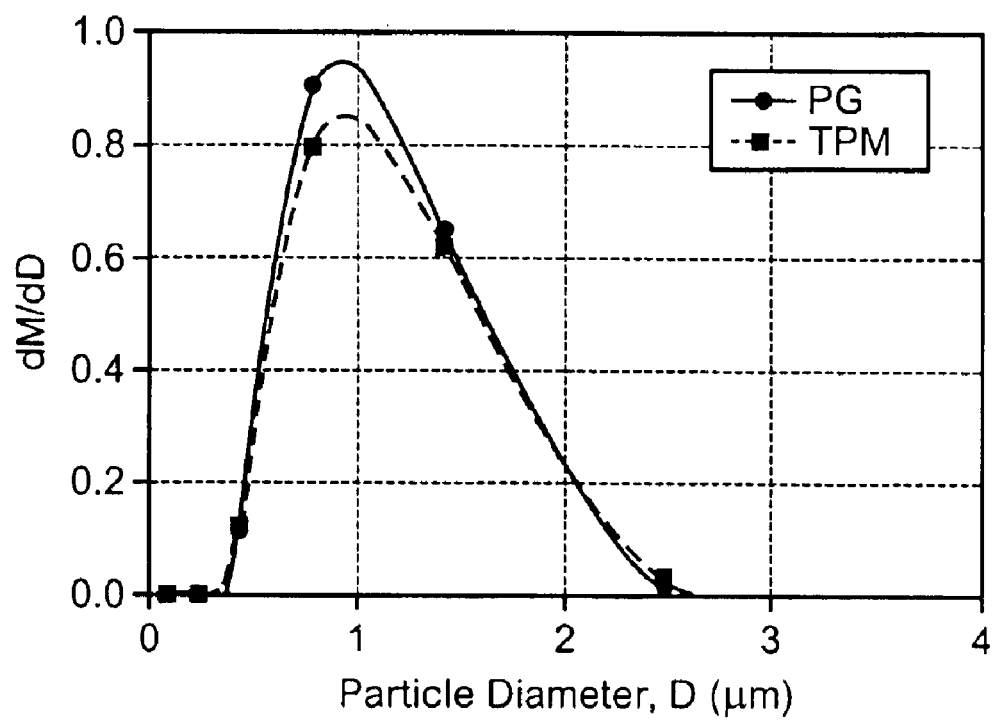
FIG. 21 is a graph illustrating a chemical distribution for propylene glycol and triphenylmethane as a function of particle diameter showing behavior when a solute and a vehicle have equivalent vapor pressures.

A mass median aerodynamic diameter (MMAD) of the aerosol produced by the aerosol generator is a function of the diameter of the heated capillary sized flow passage and the input flow rate. FIG. 20 presents exemplary MMAD plotted as a function of the PG flow rate for several capillary diameters. The data shown with reference to FIG. 21 reflects PG without solute. As the flow rate increases, the MMAD of the aerosol first decreases, then it levels off to a constant value. As the capillary diameter increases, the particle size for the entire flow rate range also increases. In an exemplary embodiment, these two effects can be used to tailor the MMAD of the aerosol.

Adding a solute, such as a drug, to the PG can change the condensation process because the solute may act as nucleating agent for the PG. If the solute has a vapor pressure similar to the PG, the solute condenses in the aerosol at the same time that the PG condenses. When 0.28 weight % of triphenylmethane (TPM) is provided in PG as a carrier, TPM behaves similarly to the PG and both the TPM and the PG form an aerosol in which the TPM has the same chemical distribution as the total aerosol, as more clearly shown with reference to FIG. 21. In the graph shown with reference to the FIG. 21, the fluid feed rate was 2.5 mg/sec and the PG had a MMAD between about 1.1 µm and 1.5 µm.

Figure 22:
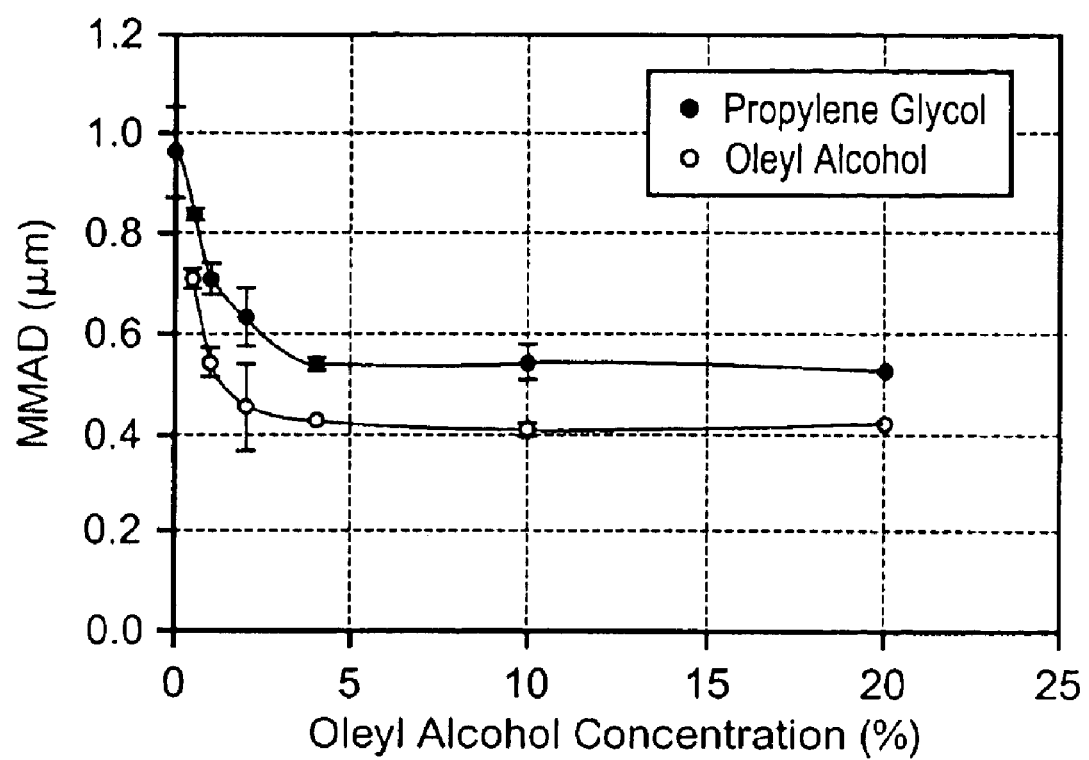
FIG. 22 is a graph showing the effect of oleyl alcohol concentration on MMAD showing behavior when a solute and liquid vehicle have different vapor pressures.

In an exemplary embodiment in which the solute is less volatile than the PG, the solute may start the condensation process early and serve as a nucleating agent for subsequent PG condensation. In this embodiment, a difference between the chemical distribution of the solute and the mass distribution of the overall aerosol may occur. This manifests itself in different MMADs for the solute and the PG. It should be noted that these are not two separate aerosols. Instead, one aerosol is produced having a varying chemical composition as a function of size. The MMADs can be a function of the solute concentration, as clearly shown with reference to FIG. 22 for oleyl alcohol (OA) in PG, due to the solute effects on the nucleation of the PG aerosol. In the embodiment shown with reference to FIG. 22, the fluid feed rate was 3.3 mg/sec. It should be noted that the presence of a solute acting as a nucleating agent for PG causes a decrease in the MMAD of the aerosol. In this embodiment, total recovery in a cascade impactor and USP induction port for OA having a 10% by weight solution was 95.1±1.2% of the amount pumped into the capillary.

The aerosol generator can be used for controlled vaporization and/or condensation of drug formulations. The aerosol generator can provide immediate delivery of aerosol to a patient, thereby not wasting lung capacity, which may be limited due to the health of the patient. Also, the aerosol generator can provide consistent delivery of controlled amounts of drug formulation to a patient.

The above are exemplary modes of carrying out the invention and are not intended to be limiting. It will be apparent to those of ordinary skill in the art that modifications thereto can be made without departure from the spirit and scope of the invention as set forth in the accompanying claims. For instance, while a heated capillary tube has been described as the preferred construction of the capillary passage, the capillary passage can comprise one or more channels in a laminate having a heater arranged along the channel(s), multiple capillary tube arrangements, a passage having a heater located inside the passage, coaxial arrangements including an annular channel for fluid flow, or the like. Further, while a cammed arrangement has been described as the preferred valve operating mechanism, individual solenoid valves or other suitable valve actuating arrangements can also be used.

What is claimed is:

1. An aerosol generator, comprising:
 a reservoir containing a liquid;
 a flow passage in fluid communication with the reservoir; and
 a heater arranged to heat the liquid in the flow passage to produce a vapor, the vapor admixing with air to produce an aerosol;
 wherein:
  a) the reservoir comprises a chamber, a liquid stored in a bladder in the chamber, and a free weight which compresses the bladder such that the liquid can be subjected to substantially constant pressure;
  b) the reservoir is removably attachable to a fluid delivery assembly of the aerosol generator;
  c) the flow passage is defined by an elastomeric member which comprises at least a first depression which defines a metering chamber, the first depression being sized to contain a predetermined volume of the liquid; and/or d) the flow passage is defined by an elastomeric member which comprises a first depression which defines a metering chamber, a second depression which defines an inlet valve, and a third depression which defines an outlet valve.

2. The aerosol generator of claim 1, further comprising a capillary passage in fluid communication with the metering chamber, a motor and a camshaft, the camshaft including a plurality of camshaft lobes operatively associated with the first depression, second depression and third depression, the camshaft lobes being operable to close the inlet valve, open the outlet valve and compress the metering chamber during an aerosol delivery cycle in which liquid is supplied to the capillary passage.

3. The aerosol generator of claim 2, wherein the camshaft lobes are operable to open the inlet valve and close the outlet valve during a fill cycle in which fluid is supplied to the metering chamber.

4. The aerosol generator of claim 2, further comprising a stepper motor operatively coupled with the camshaft, the stepper motor rotating the camshaft to open and close the inlet valve and outlet valve.

5. The aerosol generator of claim 2, further comprising a dispensing piston which engages the elastomeric member during the aerosol delivery cycle.

6. The aerosol generator of claim 2, further comprising a power supply and a controller, the controller being operable to monitor a parameter of the heater and deliver power from the power supply to the heater such that the heater is maintained at a desirable temperature range during the aerosol delivery cycle.

7. The aerosol generator of claim 1, further comprising a controller and a pressure sensor, the pressure sensor being operable to send the controller a signal when the user inhales on an outlet of a mouthpiece.

8. The aerosol generator of claim 7, wherein the pressure sensor is operable to detect a pressure drop in an interior of the mouthpiece when the user inhales on the outlet of the mouthpiece.

9. The aerosol generator of claim 1, wherein the aerosol generator is a hand-held inhaler including a mouthpiece having an interior and an outlet and a pressure sensor, the interior of the mouthpiece is supplied air only through an air passage, and the aerosol generator further comprises a drive assembly which actuates the inlet valve and outlet valve within a predetermined time period after the pressure sensor detects a pressure drop in the interior of the mouthpiece as the user inhales on the outlet.

10. The aerosol generator of claim 1, wherein the liquid is a liquid medicament comprising a drug and a carrier and the aerosol generator is a hand held inhaler.

11. An aerosol generator, comprising:
a reservoir comprising a chamber, a liquid stored in a bladder in the chamber, and a free weight which compresses the liquid such that the liquid can be subjected to substantially constant pressure;
a flow passage in fluid communication with the reservoir; and
a heater disposed to heat a portion of the flow passage to produce a vapor, the vapor admixing with air to produce an aerosol.

12. The aerosol generator of claim 11, wherein the weight applies the substantially constant pressure to an outer surface of the bladder.

13. The aerosol generator of claim 11, wherein the reservoir is open to the atmosphere.

14. The aerosol generator of claim 11, wherein the weight is sized relative to the chamber so that the weight is constrained to move slidably in the chamber along a rectilinear path.

15. The aerosol generator of claim 11, wherein the weight has a spherical configuration.

16. The aerosol generator of claim 11, further comprising a flow conduit which penetrates a wall of the bladder and is fluid communication with the flow passage.

17. The aerosol generator of claim 11, further comprising a capillary passage in fluid communication with a metering chamber of the flow passage, a motor, a camshaft, an inlet valve, an outlet valve, the camshaft including a plurality of camshaft lobes operatively associated with the inlet valve, the outlet valve and the metering chamber, the camshaft lobes being operable to close the inlet valve and open the outlet valve and compress the metering chamber during an aerosol delivery cycle in which liquid is supplied to the capillary passage.

18. The aerosol generator of claim 17, wherein the camshaft lobes are operable to open the inlet valve and close the outlet valve during a fill cycle in which fluid is supplied to the metering chamber.

19. The aerosol generator of claim 17, further comprising a stepper motor operatively coupled with the camshaft, the stepper motor rotating the camshaft to open and close the inlet valve and outlet valve.

20. The aerosol generator of claim 11, further comprising a controller and a pressure sensor, the pressure sensor being operable to send the controller a signal when the user inhales on an outlet of a mouthpiece.

21. The aerosol generator of claim 11, wherein the liquid is a liquid medicament comprising a drug and a carrier and the aerosol generator is a hand held inhaler.

22. An aerosol generator, comprising:
a reservoir containing a liquid, the reservoir being removably attachable to a fluid delivery assembly of the aerosol generator;
the fluid delivery assembly including a flow passage and a heater, the flow passage being in fluid communication with the reservoir, the heater being arranged to heat the liquid in the flow passage to create a vapor which admixes with air to produce an aerosol.

23. The aerosol generator of claim 22, wherein the fluid delivery assembly is removably attachable to the aerosol generator.

24. The aerosol generator of claim 22, further comprising a drive assembly which is operably associated with the fluid delivery assembly to cause the liquid to move through the flow passage.

25. The aerosol generator of claim 24, further comprising control electronics, a mouthpiece and a pressure sensor, the pressure sensor being operable to detect a pressure drop caused by a user inhaling on the mouthpiece, the control electronics activating the drive assembly and the fluid delivery assembly so as to generate the aerosol when the pressure sensor detects a predetermined pressure drop.

26. The aerosol generator of claim 24, further comprising control electronics and a manually activated switch, the control electronics activating the drive assembly and fluid delivery assembly so as to generate the aerosol when a user activates the switch.

27. The aerosol generator of claim 24, wherein the fluid delivery assembly and the drive assembly are removably attached to each other by a snap-fit or twist-on engagement.

28. The aerosol generator of claim 22, wherein the liquid is a liquid medicament comprising a drug and a carrier and the aerosol generator is a hand held inhaler.

29. The aerosol generator of claim 28, wherein the liquid medicament is contained in a bladder in the reservoir.

30. An aerosol generator, comprising:

a reservoir containing a liquid;

a flow passage in fluid communication with the reservoir, the flow passage being defined at least in part by an elastomeric member, the elastomeric member including a depression defining a metering chamber sized to contain a predetermined volume of the liquid;

a capillary passage in fluid communication with the metering chamber; and a heater arranged relative to the capillary passage so as to heat at least a portion of the capillary passage sufficiently to volatilize liquid contained in the portion of the capillary passage.

31. The aerosol generator of claim 30, wherein the elastomeric member comprises an elastomeric membrane which extends between inlet and outlet ends of the flow passage.

32. The aerosol generator of claim 30, further comprising a depression actuator operatively associated with the depression, the depression actuator being movable to deform the elastomeric material so as to remove liquid contained in the metering chamber.

33. The aerosol generator of claim 32, further comprising a rotatable camshaft including a lobe operably associated with the depression actuator to move the depression actuator.

34. The aerosol generator of claim 32, further comprising an inlet valve operable to allow liquid to enter the flow passage from the reservoir, and an outlet valve operable to allow liquid to enter the capillary passage.

35. The aerosol generator of claim 34, further comprising an inlet valve actuator which is operable to open and close the inlet valve, and an outlet valve actuator which is operable to open and close the outlet valve.

36. The aerosol generator of claim 35, wherein the camshaft further comprises lobes operably associated with the inlet valve actuator and the outlet valve actuator to open the inlet valve, close the outlet valve, and maintain the metering chamber in a condition to be filled by the liquid.

37. The aerosol generator of claim 36, wherein the camshaft is operable to close the inlet valve, open the outlet valve, and compress the metering chamber to deliver the liquid from the metering chamber into the capillary passage.

38. The aerosol generator of claim 30, wherein the liquid is a liquid medicament comprising a drug and a carrier and the aerosol generator is a hand held inhaler.

39. An aerosol generator, comprising:

a reservoir containing a liquid;

a flow passage in fluid communication with the reservoir, the flow passage being defined at least in part by an elastomeric member, the elastomeric member comprising first, second and third depressions, the first depression comprising an inlet valve, the second depression comprising an outlet valve, and the third depression defining a metering chamber sized to contain a predetermined volume of the liquid;

a capillary passage in fluid communication with the metering chamber; and a heater arranged relative to the capillary passage so as to heat at least a portion of the capillary passage sufficiently to volatilize liquid contained in the portion of the capillary passage.

40. The aerosol generator of claim 39, wherein the first, second and third depressions each have a dome shape.

41. The aerosol generator of claim 39, wherein the elastomeric member comprises an elastomeric membrane which extends between inlet and outlet ends of the flow passage.

42. The aerosol generator of claim 39, further comprising a first actuator operatively associated with the first depression, a second actuator operatively associated with the second depression, and a third actuator operatively associated with the third depression, the third depression being movable by the third actuator to deform the elastomeric material so as to remove liquid contained in the metering chamber.

43. The aerosol generator of claim 42, further comprising a rotatable camshaft including a first lobe operably associated with the first actuator, a second lobe operably associated with the second actuator, and a third lobe operably associated with the third actuator.

44. The aerosol generator of claim 43, wherein the camshaft is rotatable to open the inlet valve, close the outlet valve, and maintain the metering chamber in a condition to be filled by the liquid.

45. The aerosol generator of claim 43, wherein the camshaft is rotatable to close the inlet valve, open the outlet valve, and compress the metering chamber to deliver the liquid from the metering chamber into the heater.

46. The aerosol generator of claim 39, wherein the liquid is a liquid medicament comprising a drug and a carrier and the aerosol generator is a hand held inhaler.

\* \* \* \* \*